(12) United States Patent
Roussy (10) Patent No.: US 8,514,093 B2
(45) Date of Patent: Aug. 20, 2013

(54) SIGNALING DEVICE FOR DETECTING AN OBJECT (75) Inventor: Richard Roussy, London (CA)

(73) Assignee: CHG Hospital Beds Inc. (CA)

( * ) Notice: Subject to any disclaimer, the term of this patent is extended or adjusted under 35 U.S.C. 154(b) by 0 days.

(21) Appl. No.: 13/410,223

(22) Filed: Mar. 1, 2012

(65) Prior Publication Data
US 2012/0161977 A1 Jun. 28, 2012

Related U.S. Application Data (63) Continuation of application No. 12/422,029, filed on Apr. 10, 2009, now Pat. No. 8,134,473.

(60) Provisional application No. 61/071,055, filed on Apr. 10, 2008.

(51) Int. Cl.
G08B 21/00 (2006.01)

(52) U.S. Cl.
USPC ........ 340/666; 340/667; 340/668; 340/573.1; 340/573.4; 340/650; 340/651; 340/652; 340/664; 340/640; 340/641

(58) Field of Classification Search
USPC ........... 340/666–668, 573.1, 573.4, 650–652, 340/664, 540, 541
See application file for complete search history.

(56) References Cited

U.S. PATENT DOCUMENTS

| 4,484,043 | A | 11/1984 | Musick et al. |
|---|---|---|---|
| 4,633,237 | A | 12/1986 | Tucknott |
| 5,047,602 | A | 9/1991 | Lipka |
| 5,494,180 | A | 2/1996 | Callahan |
| 5,623,760 | A | 4/1997 | Newham |
| 5,757,304 | A | 5/1998 | Redford et al. |
| 5,830,397 | A | 11/1998 | Hirmer |
| 5,843,155 | A | 12/1998 | Axelgaard |
| 5,844,488 | A | 12/1998 | Musick |
| 5,984,990 | A | 11/1999 | McDonald |
| 5,991,676 | A | 11/1999 | Podoloff et al. |
| 6,014,346 | A | 1/2000 | Malone |
| 6,121,869 | A | 9/2000 | Burgess |
| 6,208,250 | B1 | 3/2001 | Dixon et al. |
| 6,281,455 | B1 * | 8/2001 | Plottnik et al. ............. 200/61.44 |
| 6,297,738 | B1 | 10/2001 | Newham |
| 6,696,653 | B1 | 2/2004 | Smith et al. |
| 6,917,293 | B2 | 7/2005 | Beggs |
| 7,030,764 | B2 | 4/2006 | Smith et al. |
| 7,151,528 | B2 | 12/2006 | Taylor et al. |
| 7,343,807 | B2 | 3/2008 | Lorenz |
| 7,378,975 | B1 | 5/2008 | Smith et al. |

FOREIGN PATENT DOCUMENTS

| JP | 03-163619 A | 7/1991 |
|---|---|---|
| WO | 97/28989 A1 | 8/1997 |

* cited by examiner

Primary Examiner — Tai T Nguyen
(74) Attorney, Agent, or Firm — Katten Muchin Rosenman LLP (57) ABSTRACT A sheet switch (142) has a bottom layer (144) and a top layer (160). First and second conductors (148, 162) located on the bottom layer (144) form two separate conductive paths, with a voltage potential applied to the conductors (148, 162). The top layer (160) includes a ground conductor (172). Spacers (178) are positioned between the top and bottom layers (160, 144). When forces are externally applied, the spacers (178) collapse and the ground conductor (172) contacts the first and second conductors (148, 162), and establishes a conductive path therebetween.

17 Claims, 9 Drawing Sheets

SIGNALING DEVICE FOR DETECTING AN OBJECT

CROSS-REFERENCE TO RELATED APPLICATIONS

This application is a continuation of U.S. patent application Ser. No. 12/422,029, filed Apr. 10, 2009 now U.S. Pat. No. 8,134,473; which claims priority to Ser. No. 61/071,055, filed Apr. 10, 2008, the contents of which are incorporated herein by reference.

STATEMENT REGARDING FEDERALLY SPONSORED RESEARCH OR DEVELOPMENT

Not applicable.

REFERENCE TO A MICROFISHE APPENDIX

Not applicable.

BACKGROUND OF THE INVENTION

Background and Technical Field

The invention relates to signaling devices and, more particularly, to signaling apparatus for detecting the presence of an object and possible movement thereof. The method aspects of the invention relate to methods for using such signaling devices in hospital beds.

SUMMARY OF THE INVENTION

The present invention comprises a sheet switch, and the use of such a sheet switch in hospital beds. The sheet switch comprises a pair of planar sheets, having facing conductive surfaces, separated by one or more resilient compressible separators which compress under force to create contact between the conductive surfaces and close an associated circuit to provide an electronic signal.

Still further, a signaling device for detecting the presence or movement of an object includes a first top sheet with a substantially planar configuration, and a second bottom sheet having a planar configuration. One or more spacers are positioned between the first and second sheets for maintaining the sheets a predetermined distance apart. A first conductor is mounted to the first sheet, and a second conductor is mounted to the second sheet. A device establishes an electrical potential between the first conductor and the second conductor at a first level, with the sheets maintained the predetermined distance apart. The spacers at least partially collapse in response to the object exerting forces against a top of the first sheet or bottom of the second sheet, resulting from physical contact of the first conductor and second conductor. When the conductors contact each other, the electrical potential changes to a second level measurably different from the first level.

One of the facing conductive surfaces can be associated with the bottom layer sheet, and the other of the facing conductive surfaces can be associated with the top sheet. The conductive surfaces of the bottom layer can include a first conductor, and a second conductor physically spaced apart from the first conductor. The conductive surface of the top layer sheet can include a single conductive path. An electrical potential can be applied at a first level between the first and second conductors. When the separators are compressed under force, the single conductive path of the top layer will conductively contact both the first and second conductors of the bottom layer. This contact will cause the electrical potential between the first and second conductors to change from the first level to a second level, measurably different from the first level. When the electrical potential has changed to the second level, the sheet switch can be characterized as being in a closed state.

The first conductor can be in the form of a pattern of first individual conductor lines spaced apart in a parallel configuration, with a common line conductively interconnecting together the individual conductor lines. The second conductor can be in the form of a pattern of second individual conductor lines, again spaced apart in a parallel configuration. A common conductor interconnects together the second individual conductor lines. Further, the first individual conductor lines can run substantially parallel to the second individual conductor lines, with the conductor lines of the first and second conductors being interspaced on the top layer. The single conductive path can be grounded and include a series of ground conductor lines spaced apart in a parallel configuration. When the separators are collapsed as a result of externally applied forces, at least one of the ground conductor lines can electrically contact at least one of the individual conductor lines of the first conductor and at least one of the individual conductor lines of the second conductor. The conductor lines can be composed of conductive inks.

Further, the facing conductive surface of the top layer can include a first conductor, with the conductive surface of the bottom layer having a second conductor. When separators are compressed under force, the first conductor of the top layer can conductively contact the second conductor of the bottom layer. An electrical potential applied between the first and second conductors at a first level when the conductors are maintained apart will change to a second level which is measurably different from the first level upon contact of the first and second conductors. The sheet switch can then be characterized as being in a closed state. The facing conductive surface of the top layer sheet can be in the form of a sheet conductor, as well as the facing conductive surface of the bottom layer sheet. The sheet conductors can consist of conductive foil.

The sheet switch can be positioned on or adjacent a mattress of the hospital bed. Also, the switch can be positioned below the bed frame of a bed. The switch can be connected to a processor, with the processor having an input signal representative of whether the switch is in a closed or open state. The processor can generate output signals so as to generate alarms in response to the state of the sheet switch. The alarms can include one or more of the following: an alarm located at the hospital bed; an alarm located at a nurses station; a visual indication located at a nurses station. Further, the processor can generate output signals in response to the input signal from the sheet switch which will cause an operation of lighting adjacent the hospital bed. Still further, the processor can generate output signals which will cause mechanical components of the hospital bed to raise the bed a predetermined amount.

A method of monitoring the presence of a patient in a hospital bed can include placing a planar sheet contact switch on a mattress of the bed, in a position where the switch will be engaged by a person present in the bed. The method can also include placing a planar sheet contact switch below a bed frame and within crush zone areas, where a portion of the person would be injured if located on the switch during bed adjustment. Still further, the method can include the application of an electrical potential across facing conductive surfaces at a first level, when the surfaces are maintained apart. In response to external forces which are sufficient to compress the separators so as to create contact between the conductive surfaces, the electrical potential will change from the first level to a second level different from the first.

BRIEF DESCRIPTION OF THE DRAWINGS

The invention will now be described with respect to the drawings, in which.

DETAILED DESCRIPTION OF THE INVENTION

The principles of the invention will now be disclosed, by way of example, with respect to embodiments of signaling devices or sheet switches for detecting movement or the presence of objects, as illustrated in FIGS. 1-13. One preferred embodiment of the invention, makes it possible for personnel at the monitoring stations to have means for determining if a patient is entering a hospital bed, exiting the bed or has inadvertently fallen from the bed. Monitoring personnel have the capability of detecting patient movement relative, for example, to the hospital bed mattress, sheets covering the mattress, or portions of the sheets.

The preferred embodiment signaling devices are also advantageous in detecting obstacles or other obstructions to movement of structural components, as for example in motor driven hospital beds. Thus, obstacles which would impair structural movements in powered hospital beds are detected prior to the occurrence of any mechanical damage to the hospital bed components. Even more importantly, the positioning in harms way of portions of the patient or other hospital personnel operating around the hospital bed, is detected, and injury avoided.

Figure 1:
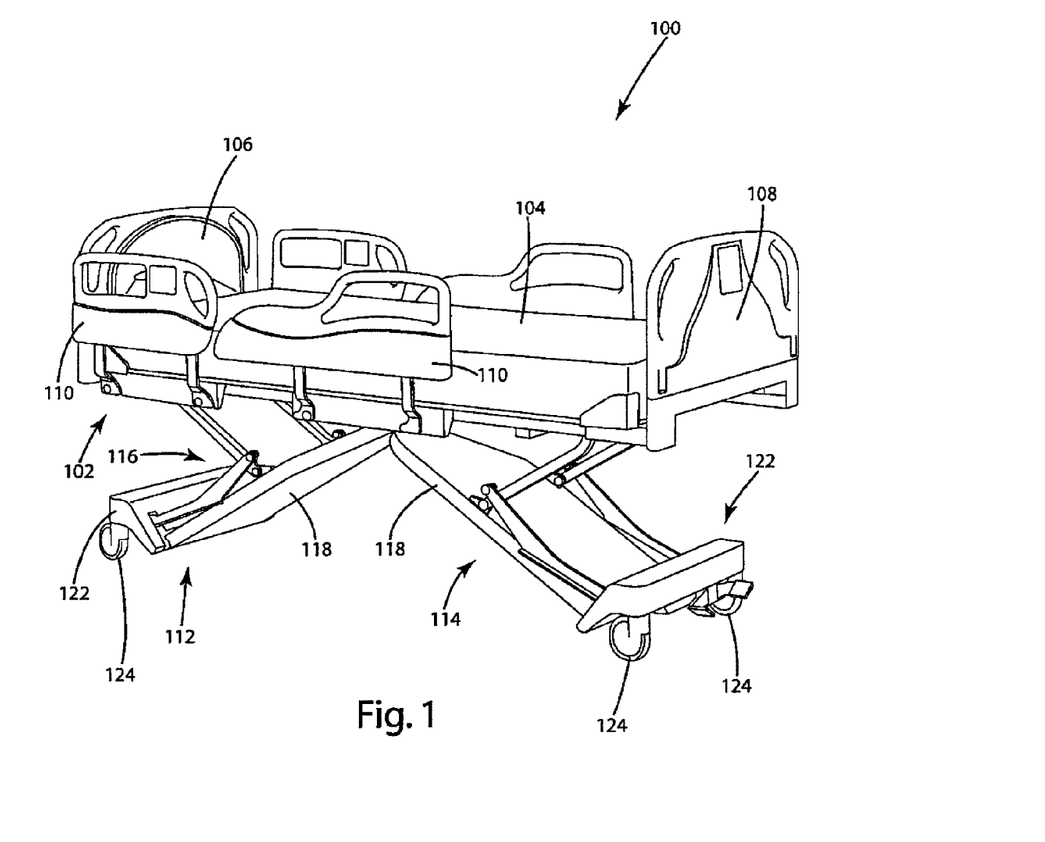
FIG. 1 is a perspective view of a hospital bed within which an embodiment of the signaling device may be utilized.
Figure 2:
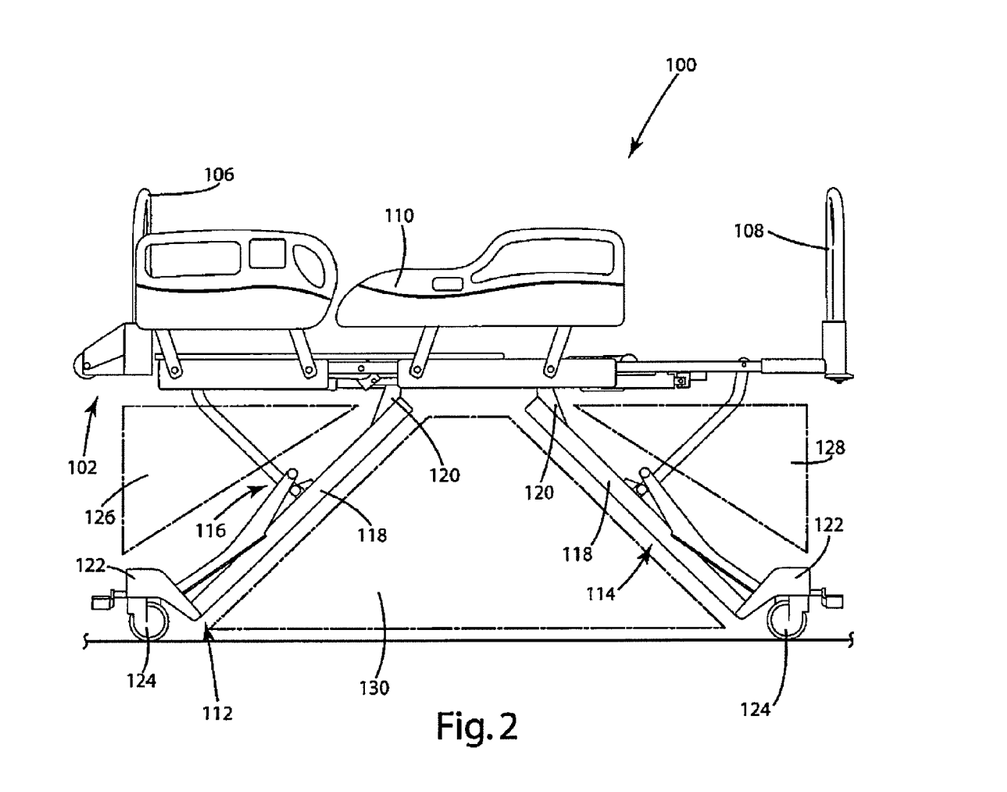
FIG. 2 is a side, elevation view of the hospital bed illustrated in FIG. 1, and is included herein to indicate what can be characterized as zones of danger or "crush zones" around mechanical components of the hospital bed.
Figure 3:
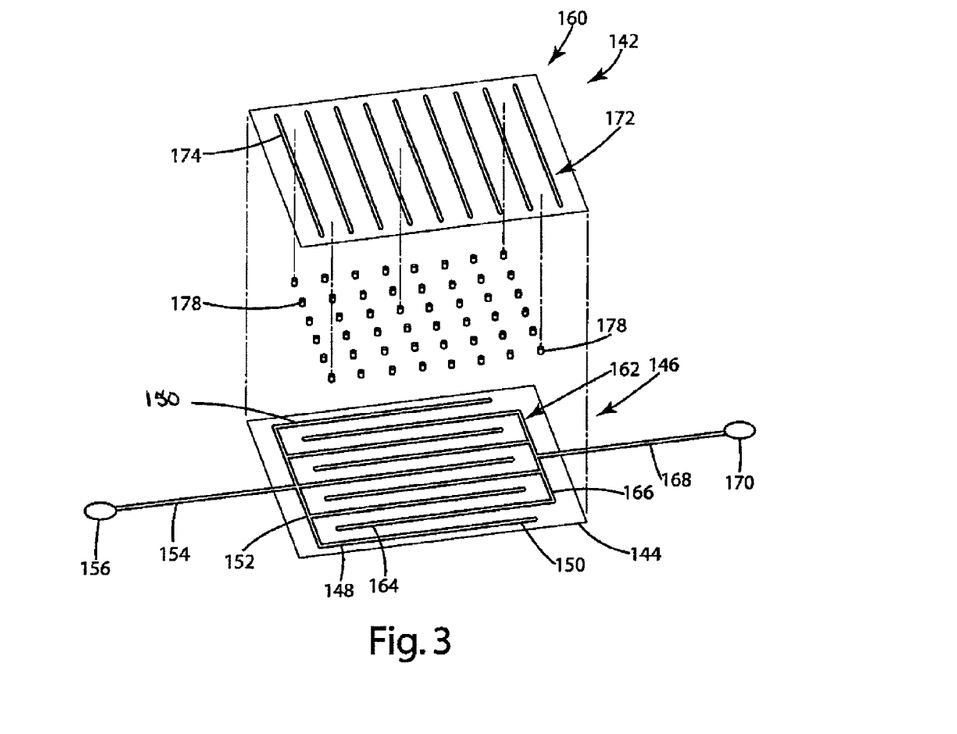
FIG. 3 is an exploded view of one embodiment of a signaling device or sheet switch.
Figure 4:
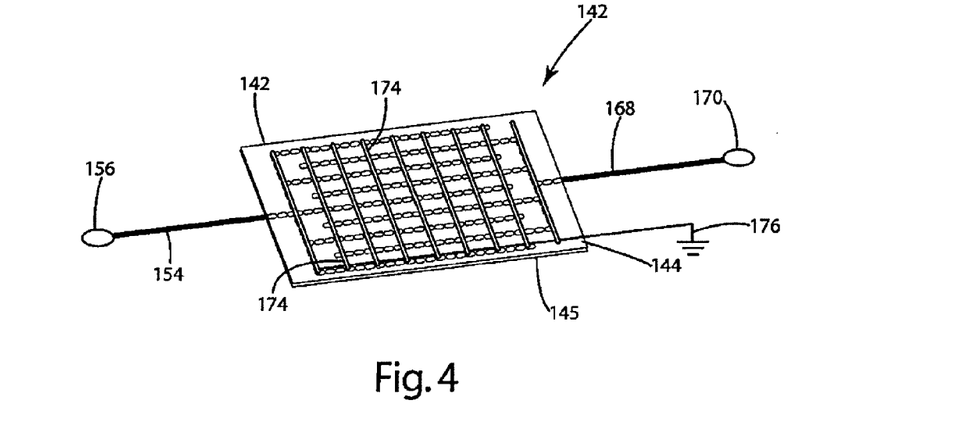
FIG. 4 is a perspective view of the sheet switch shown in FIG. 3, but shown in an assembled configuration.

To understand the features of the embodiments of the signaling devices, FIGS. 1 and 2 illustrate a hospital bed 100 having moveable components for adjusting bed height and possible other parameters of the bed configuration. The embodiments of the signaling devices as described herein may be adapted for use with the hospital bed 100. More specifically, the bed 100 can include a substantially horizontal upper frame 102, with a mattress 104 positioned thereon. At the front of the bed 100 is a conventional headboard 106, while a conventional end board 108 is connected to the upper frame 102 at the end of the bed 100. Side boards 110 are positioned on each side of the bed 100. Such side boards 110 may be moveable so as to facilitate entry and exit of a patient with respect to the bed.

The hospital bed 100 includes two leg assemblies, identified as a head leg assembly 112 and an end leg assembly 114. The leg assemblies 112, 114 include leg covers 118 which can be connected at the upper portions thereof to the upper frame 102 through slide couplings 120. The bed 100 also includes two pairs of pivot couplings 116. The pivot couplings 116 are also connected to portions of the upper frame 102. Further, the pivot couplings 116 include pivot connections to the leg covers 118, as well as to caster shields 122. The caster shields 122 are used to cover two pairs of casters 124. It should be emphasized that the hospital bed 100 is merely one example of a type of structure which may be used with the embodiments of the signaling devices described herein.

In accordance with the embodiments described herein, signaling devices can be associated with the mattress 104 (or sheet materials covering the mattress 104) so as to detect a patient's movement relative to the area of the mattress 104.

Hospital beds such as the hospital bed 100 include moving mechanical components for purposes of, for example, adjusting the height of the bed 100. In this regard, and with reference to FIGS. 1 and 2, it can be seen that motor driven forces can be applied to components such as the leg assemblies 112, 114 and slide couplings 120 so as to cause the leg covers 118 to pivot relative to the upper frame 102 through the pivot couplings 116 and slide couplings 120. With such action, and with the upper frame 102 being maintained in a horizontal configuration, the height of the upper frame 102 relative to a floor or other supporting structure can be adjusted. However, adjustment of structures such as hospital beds can be impaired by obstacles or other obstructions to movement of the mechanical components of the bed. For example, and with reference to FIG. 2, the areas marked as triangular areas 126 and 128 can be characterized as "crush zones," in that they represent areas above the leg assemblies 112, 114 and caster shields 122 where movement of mechanical components of the bed 100 is occurring during bed height adjustment. Accordingly, obstacles or other obstructions within these zones 126, 128 may substantially impair proper operation of the bed adjustment, damage bed equipment, and even be dangerous for the patient or hospital personnel physically adjacent to the bed 100. In a similar manner, another crush zone identified as crush zone 130 exists in an area which is below the leg covers 118. As the upper frame 102 of the hospital bed 100 is lowered, the leg covers 118 will essentially "flatten out," with the area between the lower surfaces of the leg covers 118 and the floor being continuously reduced.

For purposes of providing detection of movement of a patient relative to different locations associated with the mattress 104, and for purposes of detecting the presence of obstacles or other obstructions to motor driven movement of mechanical components of the bed 100 when the height or other positions of the bed 100 is being manipulated, a signaling device 140 can be utilized. One embodiment of the signaling device 140 is illustrated in FIGS. 3-7 as sheet switch 142. A concept associated with the sheet switch 142 is the generation of a switched electrical signal in response to contact across at least a limited area by another entity. The other entity could be a moving patient in the case of the sheet switch 142 being associated with one or more areas of mattress 104 (or locations adjacent thereto), where a patient may contact the sheet switch 142 when entering or exiting the hospital bed 100. Further, the sheet switch 142, as described in subsequent paragraphs herein, can be positioned on other components of the hospital bed 100, so as to provide for a switched signal in response to such other components contacting an obstacle or other type of obstruction.

Referring to the drawings, the sheet switch 142 can consist of a bottom layer or sheet 144 and top layer or sheet 160. The bottom layer 144 of the sheet switch 142 consists of what can be characterized as an electrified grid 146. The electrified grid 146 includes a first conductor 148. The conductor 148 can be a pattern of individual conductor lines 150 which are spaced apart in a parallel configuration. A common conductor line 152 can run perpendicular to the individual conductor lines 150 and conductively interconnect together the individual lines 150. In this manner, a continuous conductive path is formed by the first conductor 148. The first conductor 148, and other conductor lines described herein, can be formed through the use of conductive inks. The conductive inks can be then formed on the bottom layer 144 through the use of silk screening in a desired pattern. The bottom layer 144 itself can be a substrate sheet formed from a suitable plastic material, such as ABS. One end of the common conductor line 152 can be connected in a suitable manner to a first cable 154, which can be in the form of a ribbon cable or the like. The first cable 154 can then be connected to a suitable first connector or terminal 156.

Figure 5:
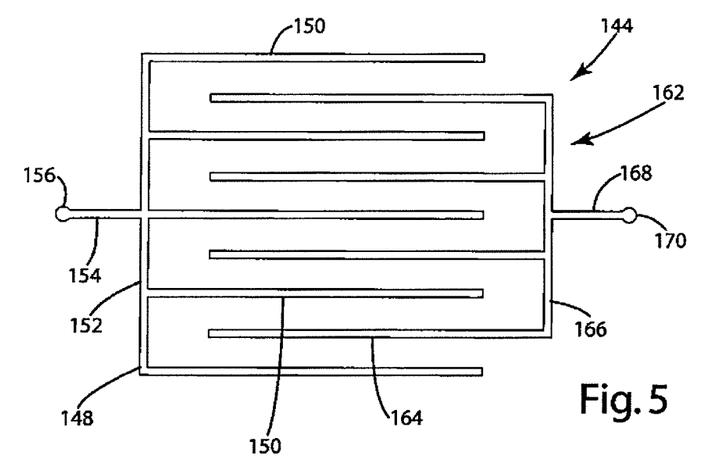
FIG. 5 is a planar and diagrammatic view of a bottom layer of the sheet switch shown in FIG. 4, and particularly showing the conductor configurations.

Referring in particular to FIG. 5, the electrified grid 146 of the bottom layer 144 of the sheet switch 142 further includes a second conductor 162. The second conductor 162 can be in a pattern of second individual conductor lines 164. The second individual conductor lines 164, like the first individual conductor lines 150, are individually spaced apart in a parallel configuration. As further shown, the second individual conductor lines 164 also run parallel to the first individual conductor lines 150, with each of the second individual conductor lines 164 interspaced between two adjacent first individual conductor lines 150. A second common conductor line 166 can run perpendicular to the second individual conductor lines 164 and conductively interconnect together the lines 154. In this manner, a continuous conductive path is formed by the second conductor 162. As also shown in FIG. 5, the second common conductor line 166 can run essentially parallel to the first common conductor line 152, and can be located on an opposing side of the bottom layer 144 from a side on which the first common conductor line 152 is located. One end of the second common conductor line 166 can be connected in a suitable manner to a second cable 168, which can be in the form of a ribbon cable or the like. The second cable 168 can then be connected to a suitable second connector or second terminal 170. In accordance with the foregoing, the continuous conductive path formed by the first conductor 148 is physically and electrically separate from the continuous conductive path formed by the second conductor 162. Further, the first individual conductor lines 150 and second individual conductor lines 164 are sufficiently spaced apart so as to ensure that there is no spatial conductivity between adjacent ones of the lines 150 and 164, given the voltage potentials (described subsequently herein) which may be applied to the first and second conductors 148, 162, respectively. An adhesive 145 can be applied to the bottom of the bottom layer 144, for purposes of securing the switch 142 to portions of the bed 100.

Reference is now made to FIGS. 3, 4, 6 and 7, which illustrate the top layer 160 of the sheet switch 142. As particularly shown in FIGS. 3 and 6, the top layer 160 includes a ground conductor 172. The ground conductor 172 includes a series of ground conductor lines 174, with the conductor lines 174 spaced apart in a parallel configuration. The ground conductor lines 174 are commonly interconnected to a common ground representatively shown as ground path 176. As further shown in FIG. 3 in an exploded format, the top and bottom layers 160, 142, respectively are maintained in a physically separate configuration by a series of collapsible and/or compressible spacers (which can be characterized as resilient separators) 178. The spacers 178 can be formed of a suitable material which is composed of appropriate compressible or collapsible material which will substantially collapse when forces are exerted on one or both ends of the spacers 178. Such material may consist of polyester, polycarbonate, or materials of similar properties.

Figure 11:
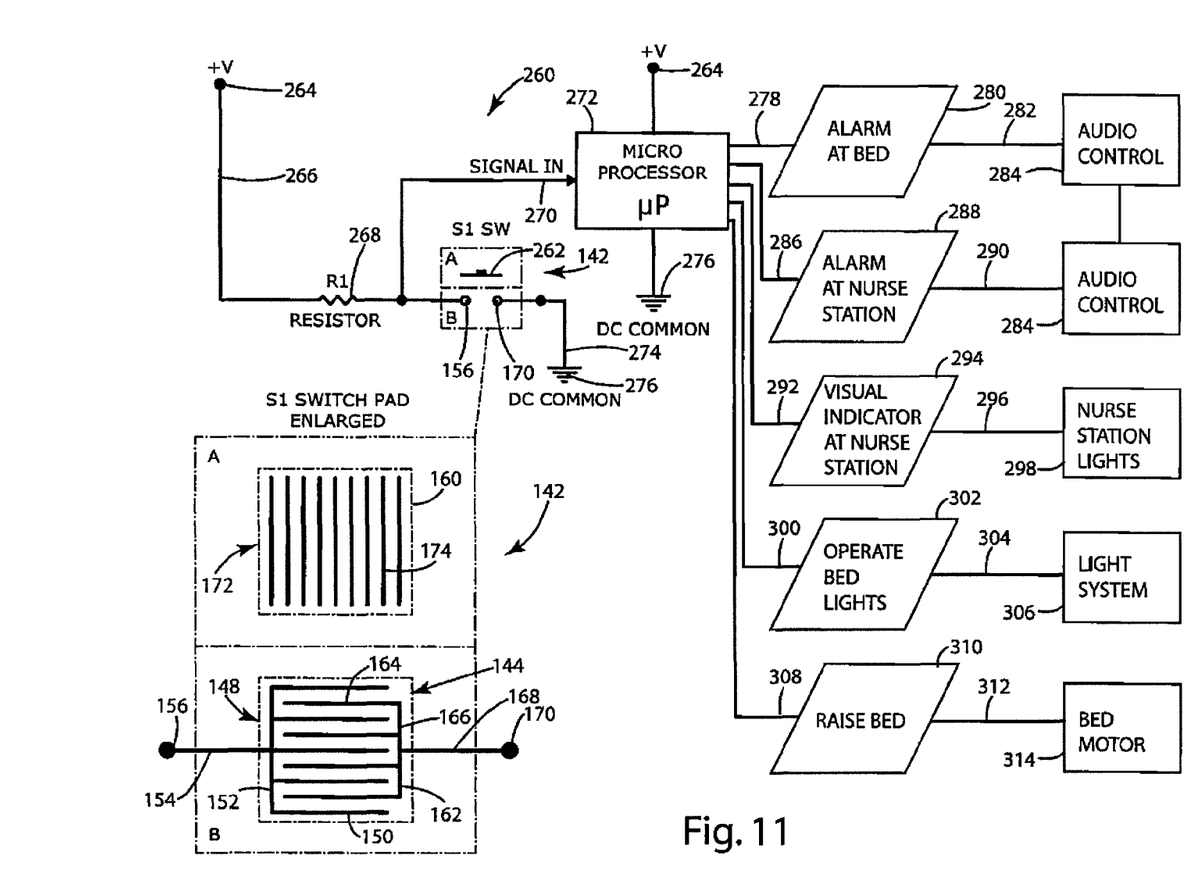
FIG. 11 is a partially schematic and partial circuit block diagram of an embodiment of a switching circuit which can be used with the three embodiments of the sheet switch.

When the sheet switch 142 is in use, a voltage or electrical potential can be applied between the first connector 156 and the second connector or terminal 170. The application of this voltage potential across connectors 156, 170 will correspondingly cause a voltage potential to exist between the first conductor 148 and the second conductor 154. With this potential across the conductors 148, 162, the sheet switch 142 can be characterized as being in an "open" state. The electrical potential can be applied through a battery or other desired power source. For purposes of illustration, the terminal 264 having a "+V" symbol (for voltage potential) in FIG. 11 represents a battery or other power source.

Figures 6, 7:
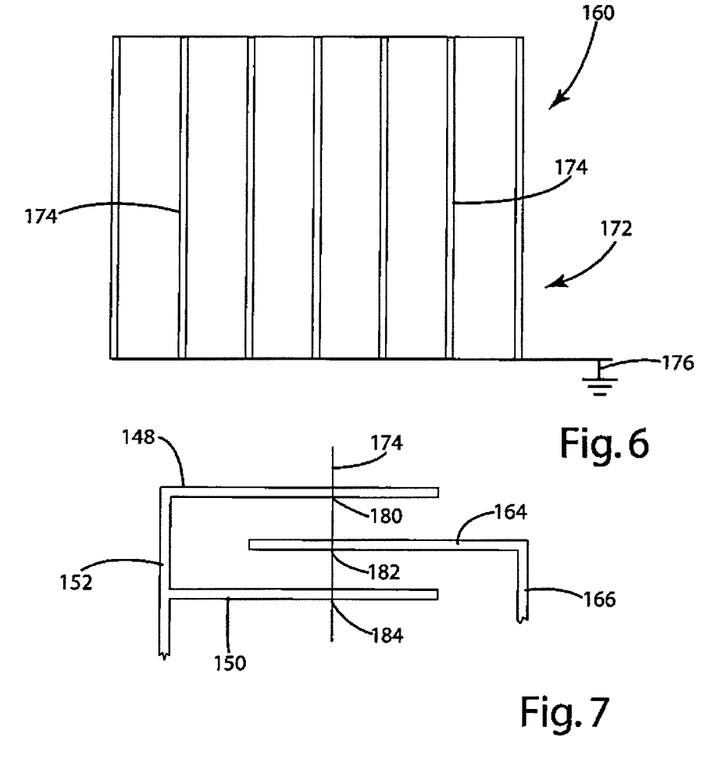
FIG. 6 is a planar and diagrammatic view of the top layer of the sheet switch shown in FIG. 4.
FIG. 7 is an enlarged view of a portion of the sheet switch shown in FIG. 4.

If the sheet switch 142 (along with a series of other sheet switches 142) is used on or adjacent the mattress 104 of the hospital bed 100, it can provide for detection of movement of a patient into or out of the hospital bed 100, or to detect other patient movement. In the event of such movement, the patient's actions will cause the patient to contact the top layer 160 of the sheet switch 142. This contact will correspondingly exert forces on the top layer 160 and the spacers 178 positioned between the top layer 160 and the bottom layer 144. These forces, in turn, will cause one or more of the spacers 178 to compress or collapse. This collapsing of the spacers or separators 178 will result in the top layer 160 moving toward the bottom layer 144. With sufficient movement, one or more of the ground conductor lines 174 will contact one or more of the first individual conductor lines 150 and one or more of the second individual conductor lines 164. With the ground conductor lines 174 in contact with lines 150, 164, a conductive path will be established between the first and second conductors 148, 162, respectively. With the establishment of this conductive path, and assuming low resistance in the conductive paths, the voltage potential between the first connector 156 and the second connector 170 will essentially drop to zero. In fact, even if there is more than just minimal resistance within the conductive paths, the voltage potential existing between the first connector 156 and the second connector 170 will measurably change upon contact of the ground conductor 172 with the conductors 148, 162, assuming that a sufficient potential originally existed between the connectors 156, 170. With the ground conductor 172 establishing a conductive path between the first and second conductors 148, 162, respectively, the sheet switch 142 can be characterized as being in a "closed" state. In this regard, FIG. 7 is an enlarged view of a portion of the sheet switch 142 when one of the ground conductor lines 174 is in contact with two of the first conductors 148 and one of the second conductors 162, which is spaced intermediate the two contacted first conductors 148. These contacts are shown as being made at locations 180, 182 and 184.

In accordance with the embodiment comprising the sheet switch 142 as illustrated in FIGS. 3-7, the sheet switch 142 can be used as a means for electrically detecting the exertion of forces on the sheet switch 142 from an external entity. In this particular embodiment, the sheet switch 142 includes a bottom layer 144 having a pair of conductors which will "normally" have an electrical potential existing across the conductors, absent extremely applied forces. A separate top layer 160 includes a ground conductor 172. When external forces are applied to the top layer 160, the layer 160 will collapse against the bottom layer 144. This collapsing action will cause the ground conductor 172 to physically contact one or more portions of the first conductor 148 and the second conductor 162. This contact will establish a conductive path between the conductors 148, 162, which can essentially be characterized as "closing a switch" between the conductors. Even with some resistance within the conductors 146, 162 and 172, the electrical potential between the conductors 148, 162 will be substantially reduced. Accordingly, this conductor configuration of the sheet switches 142 can essentially establish a "binary" switch. The binary switch can be characterized as having a normally "open" configuration, in the absence of externally applied forces. In the presence of externally applied forces, the binary switch will essentially be converted to what can be characterized as a "closed" state.

Further in accordance with the foregoing description, the conductors 148, 162 on the bottom layer 144 and the conductor 172 on the top layer 160 can be characterized as "facing conductive surfaces." When contact is made, the action can be characterized as closing an associated circuit so as to provide an electronic or electrical signal.

An alternative embodiment of a signaling device and sheet switch is illustrated in FIGS. 8, 8A, 8B and 9 as sheet switch 202. With the sheet switch 142, first and second conductors 148, 162, respectively were both incorporated on the bottom layer 144 and, absent contact with the top layer 160, maintain a voltage differential between the conductors. The switch 142 was essentially "closed" when the ground conductor 172 made contact with both the first and second conductors 148, 162. In contrast, the sheet switch 202 essentially includes one "side" of the switch being mounted to one layer thereof, while the "other side" of the switch (which can be at ground potential) is located on the other layer.

Figure 8:
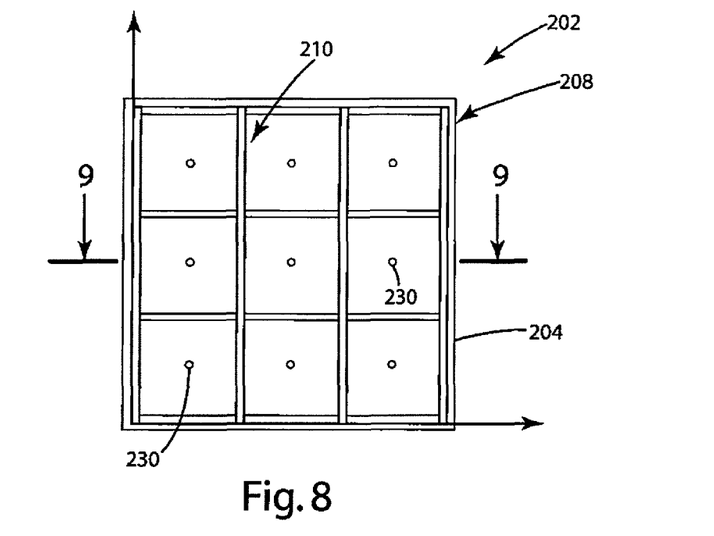
FIG. 8 is a planar and diagrammatic illustration of a second embodiment of the sheet switch or signaling device.
Figure 8A:
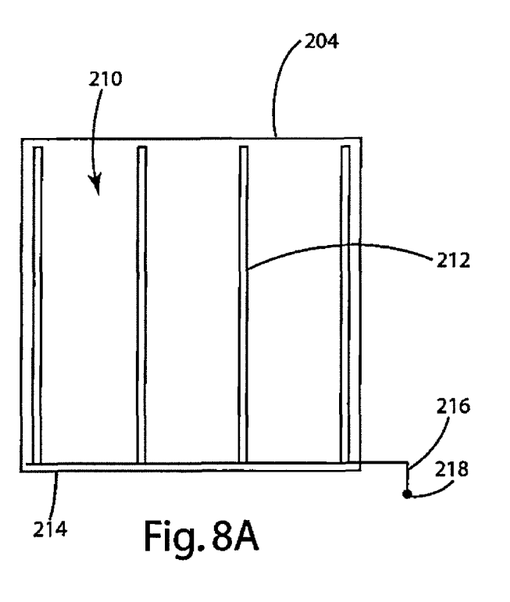
FIG. 8A is a planar and diagrammatic view of the top layer of the sheet switch shown in FIG. 8.
Figure 8B:
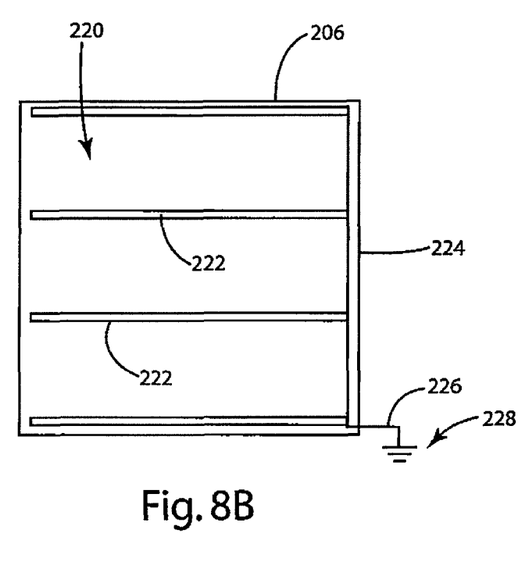
FIG. 8B is a planar and diagrammatic view of the bottom layer of the sheet switch shown in FIG. 8.

More specifically, the sheet switch 202 includes a top layer 204 (shown separately in FIG. 8A) and a bottom layer 206 (shown separately in FIG. 8B). When viewed from above, as in FIG. 8, the conductors of the layers form what can be characterized as an electrified grid 208. Referring specifically to the top layer 204, the layer includes a first conductor 210. The conductor 210 can be formed in a pattern of individual first conductor lines 212 which, in this particular embodiment, are shown as being individually spaced apart in a parallel configuration. A first common conductor line 214 can run perpendicular to the individual conductor lines 212 at one end thereof, and conductively interconnect the lines together. In this manner, a continuous conductive path is formed by the first conductor 210. As previously described with respect to the sheet switch 142, the conductor lines can be formed in a pattern through the use of silk screening with conductive inks. Further, the top layer 204 can be formed as a substrate sheet from a suitable plastic material, such as ABS. One end of the common conductor line 214 can be connected in a suitable manner to a first cable 216. The cable 216 can be connected to a first connector or terminal 218.

With reference now primarily to FIG. 8B, the bottom layer 206 includes a second conductor 220. If desired, the second conductor 220 can be at a ground potential. The second conductor 220 can be a conductive sheet or, alternatively, can be in the form of second individual conductor lines 222. The second individual conductor lines 222, like the first individual conductor lines 212, can be individually spaced apart in a parallel configuration. Further, the second individual conductor lines 222 can be configured so as to have their longitudinal axes running in a direction having a 90° differential from the direction of the longitudinal axes of the first individual conductor lines 212 of the top layer 204. A second common conductor or ground line 224 can run perpendicular to the second individual ground conductor lines 222 and conductively interconnect them together. In this manner, a continuous conductive path is formed by the second conductor or ground conductor 220. As further shown in FIG. 8B, one end of the second common conductor or ground line 224 can be connected in a suitable manner to a second cable 226. In turn, the cable 226 can then be connected to a suitable second or ground connector 228.

Figure 9:
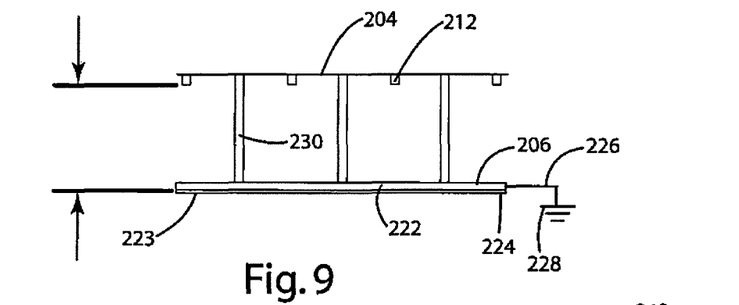
FIG. 9 is a partial and side, elevation view of the sheet switch shown in FIG. 8, taken along section lines 9-9 of FIG. 8.

With reference primarily to FIGS. 8 and 9, and in a manner similar to the previously described sheet switch 142, the top layer 204 and bottom layer 206 of the sheet switch 202 are spaced apart through the use of individual spacers 230 which can be positioned in any of a number of suitable patterns, and coupled to the bottom of the top layer 204 and the top of the bottom layer 206. As earlier described, the spacers 230 may be composed of a polyester or polycarbonate material. The spacers can be positioned around the parameter of the top and bottom layers 204, 206, respectively, as well as in a suitable design for ensuring detection of forces exerted on the sheet switch 202. As previously described with respect to the sheet switch 142, the spacers 230 of the sheet switch 202 are designed so as to collapse upon the application of external forces to the sheet switch 202, resulting in the top layer 204 contacting the bottom layer 206. As with switch 1142, an adhesive 223 can be applied to the bottom of the bottom layer 206 to secure the switch 202 to portions of the bed 100.

When the sheet switch 202 is in use, a voltage potential (being non-zero relative to ground) can be applied to the first conductor 210 through the first connector 218. Application of this voltage potential to the first connector 218 will correspondingly cause a voltage potential to exist between the first conductor 210 and the second ground conductor 220. With this potential across the conductors 210, 220, the sheet switch 202 can be characterized as being in an "open" state.

Figure 12:
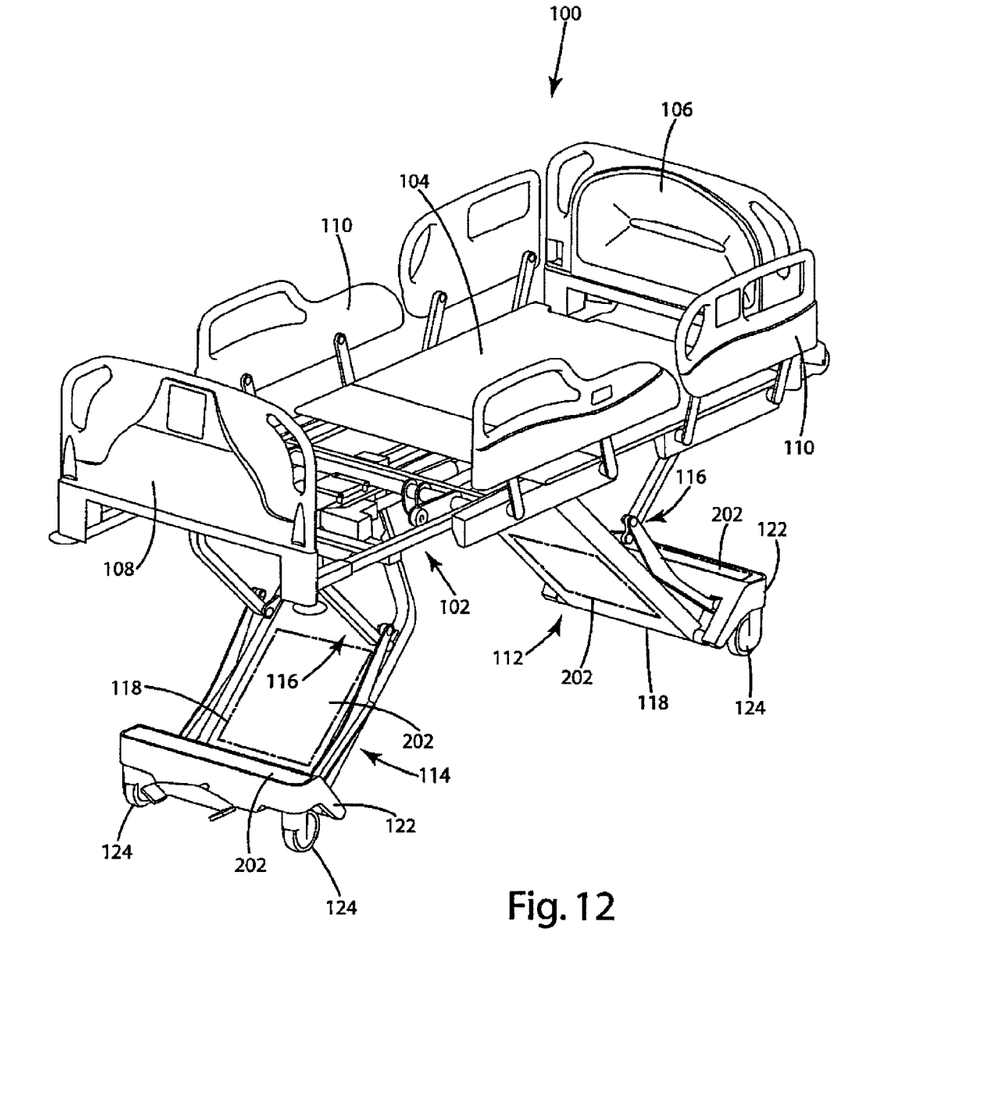
FIG. 12 is a perspective view of the hospital bed illustrated in FIGS. 1 and 2, and showing relative positioning of three of the second embodiments of the sheet switches as mounted to a castor cover, lower leg cover and upper leg cover of the hospital bed.

The sheet switch 202 (like the sheet switch 142) can be used on or adjacent the mattress 104 of the hospital bed 100, so as to detect patient movement. The use of a sheet switch for detecting patient movement was previously discussed with respect to the switch 142. In addition to detecting patient movement, the sheet switch 202 (as well as the sheet switch 142) can also be used in various other areas of the hospital bed 100 so as to detect the existence of obstacles or other obstructions to various mechanical movements of the bed 100. For example, FIG. 12 illustrates the positioning of sheet switches on both the top and bottom portions of the leg covers 118, as well as on the caster shields 122. As previously described with respect to FIGS. 1 and 2, physical areas around the hospital bed 100 can be characterized as crush zones, such as crush zones 126, 128 and 130 previously described herein. Within these crush zones, obstacles or other types of obstructions may impair mechanical movement of the hospital bed 100. With the sheet switches 202 positioned as shown in FIG. 12, and assuming that mechanical components of the hospital bed 100 are moving so as to adjust the height or other parameters of the bed 100, obstacles or other obstructions in the crush zones would result in forces being exerted on one or more of the sheet switches 202. This contact and exertion of forces will be translated to forces applied to the top layer 204 and the spacers 230 positioned between the top layer 204 and the bottom layer 206 of one or more of the sheet switches 202. These forces, in turn, will cause one or more of the spacers 230 to collapse. This collapsing of the spacers 230 will result in the top layer 204 moving toward the bottom layer 206. With sufficient movement, one or more of the first individual conductor lines 212 will contact one or more of the second individual ground lines 222. With the ground conductor lines 222 in contact with first individual conductor lines 212, a conductive path will be established between the first conductor 210 and the second or ground conductor 220. With the establishment of the conductive path, and assuming negligible resistance in the conductive paths, the voltage potential between the first connector 218 and the ground connector 228 will essentially drop to zero. Further, even if there is more than just minimal resistance within the conductive paths, the voltage potential existing between the connectors 218, 228 will measurably change upon contact of the first conductor 210 and ground conductor 220 (assuming that a sufficient potential originally existed between the connectors 218, 228). With the first conductor 210 establishing a conductive path with the ground conductor 220, the sheet switch 202 can be characterized as being in a "closed" state. For purposes of illustration, two of the potential contact locations between the individual connector lines 212 and the individual ground lines 222 are shown in FIG. 8 as contact locations 232 and 234.

In accordance with the embodiment comprising the sheet switch 202 as illustrated in FIGS. 8, 8A, 8B and 9, the sheet switch 202 can be used as a means for electrically detecting the exertion of forces on the sheet switch 202 from an external entity. The detection occurs by action of the sheet switch 202 changing states in the event of sufficient forces being exerted. As with the sheet switch 142, the conductor configuration of the sheet switch 202 can essentially establish a "binary" switch.

Figure 10:
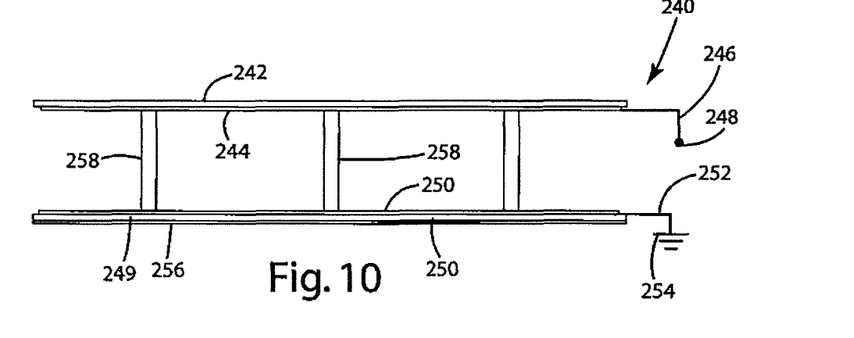
FIG. 10 is a side, elevation view of a third embodiment of the sheet switch or signaling device.

A third embodiment of a sheet switch is described herein as sheet switch 240 and is illustrated in FIG. 10. The sheet switch 240 is similar in certain respects to the sheet switches 142 and 202 previously described herein. However, the sheet switch 240 is described as including the use of conductive layers of materials, as opposed to the use of discrete conductor lines. With reference to FIG. 10, the sheet switch 240 includes a top sheet 242 which can be made of an ABS plastic or another suitable material. Attached to the lower portion of the top sheet 242 is an upper conductive layer 244. The upper conductive layer 244 is a material which essentially forms a sheet conductor. Various materials may be utilized. For example, the upper conductive layer may consist of a sheet of conductive foil material. Connected through any suitable means to the upper conductive layer 244 is a first cable 246 and a first connector 248.

The sheet switch 240 also includes a bottom sheet 249. The bottom sheet 249 can consist of an ABS plastic or similar material. On the upper portion of the bottom sheet 249, a lower conductive layer 250 is attached through any suitable means. The lower conductive layer 250 can consist of the same material as the upper conductive layer 244, such as a conductive foil material. As with the upper conductive layer 244, the lower conductive layer 250 is a sheet conductor. Electrically coupled to the lower conductive layer 250 through any suitable means is a second cable 252 and a second connector 254. For purposes of securing the sheet switch 240 to appropriate locations in or on the hospital bed 100 (or other structures), an adhesive backing 256 is secured to the outside of the bottom sheet 249. Further, to keep the upper conductive layer 244 "normally" physically apart from the lower conductive layer 250, a series of spacers 258 can be utilized. As with the previously described sheet switches, the spacers 258 are resiliently collapsible and can be made of materials such as polyester or polycarbonate. The spacers 258 can be oriented so as to surround the perimeter and can form what may be characterized as a "herringbone" design between the layers 244, 250.

When the sheet switch 240 is in use, a voltage potential can be applied between the first connector 248 and the second connector 254. The application of this voltage across the connectors will correspondingly cause a voltage potential to exist between the upper conductive layer 244 and the lower conductive layer 250. With this potential across the conductors, the sheet switch 240 can be characterized as being in an "open" state.

As with the previously described sheet switches 140, 202, the sheet switch 240 can be used on or adjacent the mattress 104 of the hospital bed 100, or it can be located on the leg covers 118 or caster shields 122 of the bed 100. When externally applied forces are exerted on the sheet switch 240, such forces can cause one or a number of the spacers 258 to collapse, and result in physical contact of the upper conductive layer 244 and the lower conductive layer 250. With this contact, a conductive path is established between the layers 244, 250. Assuming negligible resistance in the conductive paths, the voltage potential between the first connector 248 and the second connector 254 will essentially drop to zero, or otherwise be substantially reduced. With this establishment of the conductive path, the sheet switch 240 can then be characterized as being in a "closed" state. It is believed that the switch 240 may provide for a relatively "rugged" switch design.

Details regarding the use of the sheet switches for functions associated with the hospital bed 100 will now be described primarily with respect to FIGS. 11 and 13. FIG. 11 is a partially schematic and partially diagrammatic representation of the use of the sheet switches to apply signals through a processor to initiate functions associated with the hospital bed and surrounding areas, in response to detection of patient movement or the detection of obstacles or other obstructions during mechanical movement of components of the hospital bed 100. Turning specifically to FIG. 11, the drawing illustrates, in an enlarged format, one of the sheet switches 142 previously described herein. It should be emphasized that for the functions which will be described herein with respect to FIGS. 11 and 13, either of the other sheet switches 202 or 240 may also be utilized. The sheet switch 142 is shown as being incorporated within a sheet circuit 260 as a switch S1. The operation of the switch is identified by the representative switch symbol 262 further shown in FIG. 11. In the circuit 260, the first connector 156 is shown as being connected to a voltage potential V at terminal 264. The connection is made through a cable 266 and a resistor 268. The resistor 268 may represent an actual resistor or the nominal resistance which would exist within the cable 266. It should be emphasized that cable 266 and other elements described herein as "cables" or "lines" can be in the form of any suitable electrical conductors, such as ribbon cables and the like. The cables 266 and the first connector terminal 156 are also shown as being connected to an input cable 270. Input cable 270 is further shown as applying an input signal to a conventional microprocessor 272. The microprocessor 272 can be any of a number of conventional and commercially available microprocessors.

The second connector or terminal 170 of the sheet circuit 142 is further shown in FIG. 11 as being connected through a cable 274 to a ground location 276. In this manner, the voltage potential V is established between the connectors 156 and 170, absent operation of the switch 262. It should be noted that although various types of signals and voltage potentials are described herein as being designed so as to use common grounds, it would also be possible, if desired, to utilize floating potentials, although such use can be involved with various electrical disadvantages.

In accordance with the foregoing description, if external forces are applied to the sheet switch 142, a conductive path will be established between the connectors 156, 170. The establishment of this conductive path is represented by the switch 262 "closing", so as to form a conductive path between the signal existing on cable 270 and the ground 276. The input signal therefore applied to the microprocessor 272 on input cable 270 would change states. The state change will be recognized by software within the microprocessor 272.

It is apparent from the description herein that a number of sheet switches can be associated with an individual microprocessor. Accordingly, the microprocessor 272 may receive input signals from a number of different sheet switches. Either through software or pursuant to hardware port connections, software within the microprocessor 272 can be made to determine the location of the sheet switch which has changed states, relative to various portions of the hospital bed 100. For example, it would be possible to utilize port definitions or other means so as to determine whether a change of state in a sheet switch from being open to being closed occurred with respect to a switch located on or adjacent the mattress 104. Correspondingly, it can also be determined if the sheet switch which has changed states is located on the leg covers 118 or caster shields 122. Dependent upon the location of a particular sheet switch which has changed states from being open to being closed, functions associated with the microprocessor 272 can cause appropriate output signals to be generated and transmitted to various equipment associated with the hospital bed, hospital room and nurses station so as to perform certain functions. For example, and continuing to refer to FIG. 11, if it was determined that the patient was attempting to enter or exit the bed 100, signals could be applied on output line 278 which are shown in representative fashion as generating the process 280 which is directed to establishing an audio alarm at the bed 100. Either through a centralized control system or other similar means, signals can then be applied on line 282 as input signals to an audio alarm control system 284. Similarly, output signals from the processor 272 can be applied on line 286 so as to generate a process 288 for generating an alarm at the nurses station. Appropriate signals can be applied on line 290, again as input signals to the alarm control system 284.

Still further, output signals can be generated from the processor 272 on line 292 so as to generate the process 294 of providing a visual indication at the nurses station. In this regard, appropriate signals can be applied on line 296 to a nurses station lighting system 298. Output signals can also be established on line 300 from processor 272 and applied so as to generate a process 302 of operating lighting around the bed. In this regard, appropriate signals can be transmitted on line 304 as input signals to a lighting control system for the hospital room or for the bed itself. For this particular feature, it would also be possible for the processor 272 to include functions which determine whether or not there is sufficient lighting in the hospital room so that lights do not have to operate in response to operation of sheet switches.

As earlier described, sheet switches in accordance with the embodiments shown herein can be used around the lower portion of the hospital bed so as to determine obstacles or other obstructions to raising or lowering of the bed 100, or other mechanical movements. If operation of a sheet switch indicates such an obstacle has been detected, the microprocessor 272 can apply signals on output line 308, so as to cause the process 310 to be established, where the bed 100 can be made to raise a predetermined amount. For this purpose, control signals can be applied on line 312 to a bed motor control system 314. The signals would be applied so as to cause the control system 314 to raise the bed the prescribed amount.

From the foregoing description, it is clear that a number of different functions can be performed, in response to operation of the sheet switches. The sheet switches could also be used to perform other functions, based upon detection of obstacles or movement. For example, it may be possible to position a sheet switch in a particular location in a mattress, such that when the switch is activated, a sideboard adjacent the switch may be caused to be raised or lowered.

Figure 13:
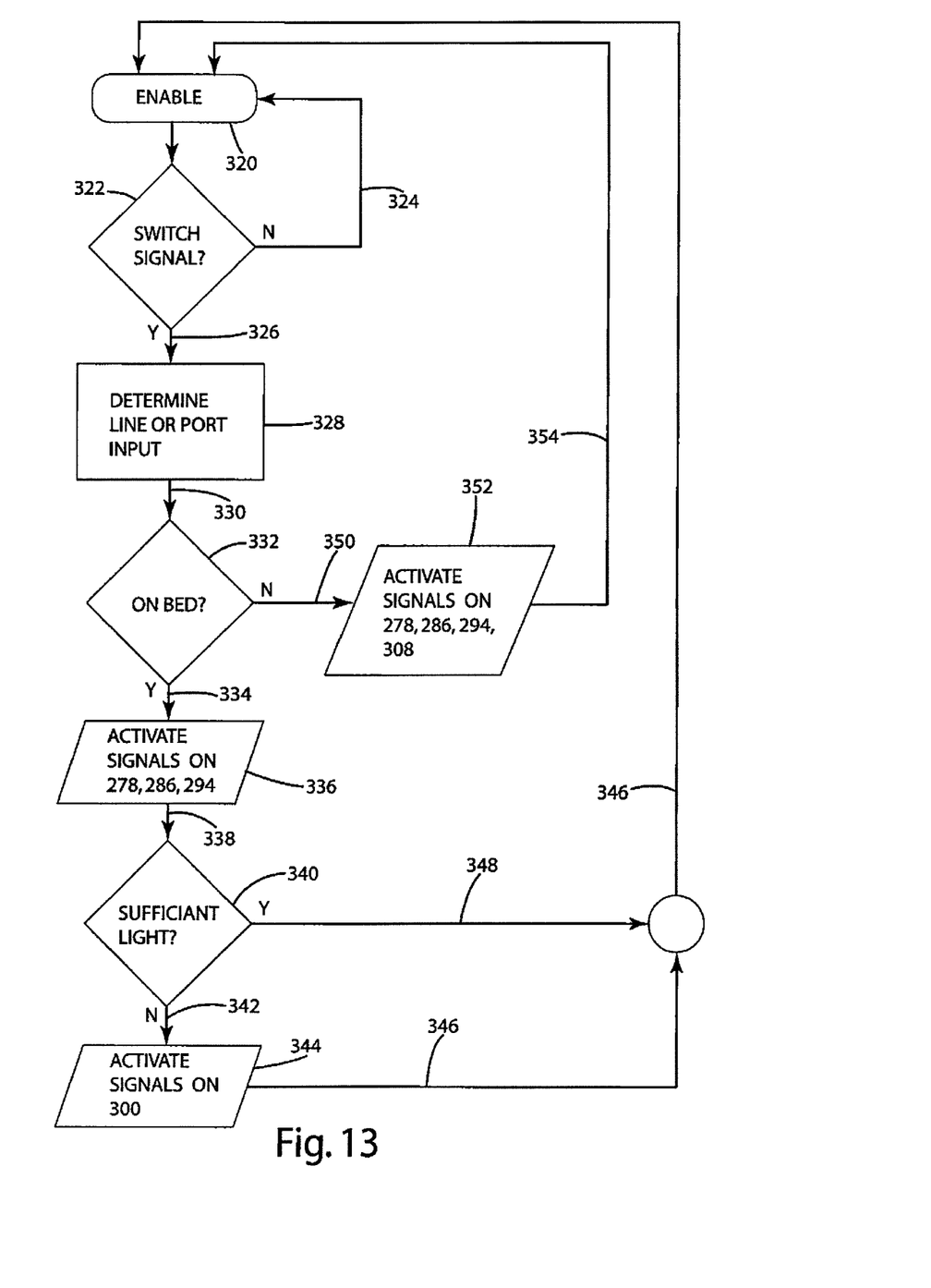
FIG. 13 is a software sequence diagram illustrating various functions which can be performed through use of the sheet switches, with respect to various features associated with the hospital bed and surrounding environment.

FIG. 13 is a sequence diagram for certain functions which maybe performed by software associated with the microprocessor 272, in response to one or more of the sheet switches being operated so as to change states. It should be emphasized that various types of functional sequences may be utilized within the software associated with processor 272.

Specifically, FIG. 13 illustrates a starting or ENABLE software location 320. At this location, an interrogation can be made of the input ports so as to determine if a sheet switch has changed states. If not, control is returned to the starting ENABLE location on control path 324. If the operation of a sheet switch has been detected, control is transferred through path 326 to a process 328 which can determine which input line or port received the sheet switch activation. In particular, this determination may be used to indicate the particular location of the sheet switch. Following this determination, control can be transferred along control path 330 to a decision process 332, where a determination is made as to whether the activated sheet switches are located on the mattress 104 or adjacent thereto. If the answer is in the affirmative, control can be transferred along path 334 so as to activate output signals on, for example, lines 278, 286 and 294 as previously described with respect to FIG. 11. These signals would cause audible and visual alarms to be activated, in accordance with prior description.

Following this action, control can be transferred along path 338 to decision process 340, where a decision is made as to whether the lighting is sufficient within the hospital room so that it is unnecessary to activate any other lighting. This can be determined in a number of different ways, with various types of known equipment. Alternatively, a determination can be made as to the time of day of the switch activation, so as to determine if sunlight would be providing sufficient light within the room. If sufficient light is not being provided, control can be transferred along path 342 to a process 344, where signals are activated on output line 300, so as to cause lights around the bed and other locations in the hospital room to be activated. Following such function, control can be returned along path 346 to the ENABLE location 320.

If sufficient light has been determined to be available through process 340, control can be directly transferred through path 348 back to the ENABLE location 320. Returning to the decision process associated with the location of the sheet switches which were operated, as determined by decision process 332, a determination may have been made that the sheet switches are located below the upper portion of the bed. In such event, control can be transferred along path 350 to process 352. In this process, signals can be activated on lines 278, 286, 292 and 308. As earlier described, signals on line 308 will cause a process 310 (FIG. 11) to transmit signals to the motor control system 314 to raise the bed a predetermined amount, or otherwise undertake other mechanical functions.

From the prior description, it is apparent that various other types of electrical and mechanical components can be utilized with the sheet switches and the hospital bed 100. For example, the hospital bed 100 may have equipment such as keypads or the like established for purposes of providing manual activation of various functions. Such keypads can be made to be associated with functions initiated by operation of the sheet switches. For example, manual functions could be provided through a keypad and associated electrical mechanical equipment so as to provide a user with the capability of deactivating various alarms or other functions which have occurred as a result of operation of the sheet switches. Still further, it is clear that other functions could be contemplated in response to operation of the sheet switches, beyond those expressly described herein.

It is worthwhile emphasizing that the sheet switch as described herein can be of particular importance in monitoring a patient's presence with respect to the hospital bed. Also, and of even greater importance, the sheet switches can be used as a method of preventing injury to a person in or near a hospital bed, while the bed is undergoing motorized adjustment. In this regard, to monitor a patient's presence, activities can be undertaken which comprise placing a planar sheet contact switch on the bed mattress, in a position where it will be engaged by a person present in the bed. Still further, for purposes of preventing injury, the activity can include placing one or more planar sheet contact switches below the bed frame in positions which may consist of crush zones, where a person would be injured if located on the switch during bed adjustment.

It will be apparent to those skilled in the pertinent arts that other embodiments of sheet switches in accordance with the invention may be designed. That is, the principles of the invention are not limited to the specific embodiments described herein. Accordingly, it will be apparent to those skilled in the art that modifications and other variations of the above-described illustrative embodiments of the invention may be effected without departing from the spirit and scope of the novel concepts of the invention.

The invention claimed is:

1. A hospital bed comprising:
   a frame for supporting a patient;
   a mechanical component attached to the frame operable to cause movement of a moving component of the bed;
   a crush zone defined between the frame and the moving component;
   a signaling device for detecting a presence of an object positioned within the crush zone said signaling device comprising,
   a first top sheet having a substantially planar configuration,
   a second bottom sheet having a substantially planar configuration,
   one or more spacers positioned between said first and said second sheets for maintaining said first and said second sheets a predetermined distance apart,
   a first conductor mounted to said first sheet,
   a second conductor mounted to said second sheet,
   a power source for establishing an electrical potential between said first conductor and said second conductor at a first level, when said first and said second sheets are maintained said predetermined distance apart,
   wherein, in response to said object exerting forces against a top of said first sheet or a bottom of said second sheet, resulting in physical contact of said first conductor and said second conductor, said electrical potential changes to a second level measurably different from said first level;
   a microprocessor on the bed configured to operably control movement of the moving component;
   wherein said change in electrical potential provides a signal indicative of the presence of an object within the crush zone to the microprocessor and wherein the microprocessor is configured to generate an output signal in response to the signal.

2. The hospital bed of claim 1, wherein the output signal stops operation of the mechanical component.

3. The hospital bed of claim 1, wherein the output signal reverses operation of the mechanical component by a predetermined amount.

4. The hospital bed of claim 1, wherein the mechanical component is motor driven.

5. The hospital bed of claim 1, wherein the output signal is delivered to a bed motor control system.

6. The hospital bed of claim 1, wherein the moving component is configured to adjust a height of the bed.

7. The hospital bed of claim 1, wherein the moving component comprises a leg of the bed.

8. The hospital bed of claim 1, wherein the output signal is configured to provide a visual indication.

9. The hospital bed of claim 1, wherein the output signal is configured to provide an audible indication.

10. The hospital bed of claim 1, wherein the signaling device is positioned below the bed frame.

11. The hospital bed of claim 10, wherein the signaling device is positioned above a leg of the bed.

12. The hospital bed of claim 10, wherein the signaling device is positioned below a leg of the bed.

13. The hospital bed of claim 10, wherein the signaling device is positioned on a caster shield of the bed.

14. The hospital bed of claim 1, wherein said first conductor comprises a plurality of spaced apart individual first conductor lines.

15. The hospital bed of claim 14, wherein said second conductor comprises a plurality of spaced apart individual second conductor lines.

16. The hospital bed of claim 15, wherein said first conductor lines are perpendicular to said second conductor lines.

17. The hospital bed of claim 1, wherein said first conductor or said second conductor comprises a conductive foil.

* * * * *